(12) United States Patent
Melder (10) Patent No.: US 8,764,777 B2
(45) Date of Patent: Jul. 1, 2014

(54) ENDOVENTRICULAR STAY AND DELIVERY SYSTEM

(75) Inventor: Robert J. Melder, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 1483 days.

(21) Appl. No.: 12/421,309

(22) Filed: Apr. 9, 2009

(65) Prior Publication Data

US 2010/0262156 A1 Oct. 14, 2010

(51) Int. Cl.
*A61B 17/08* (2006.01)

(52) U.S. Cl.
USPC .......................................... 606/155; 606/151

(58) Field of Classification Search
USPC ............... 623/23.64–23.71; 600/37; 606/151, 606/153, 156, 213, 215, 216
See application file for complete search history.

(56) References Cited

U.S. PATENT DOCUMENTS

| 2,229,936 | A | * | 1/1941 | Prache | 281/27.2 |
|---|---|---|---|---|---|
| 5,484,451 | A | * | 1/1996 | Akopov et al. | 606/139 |
| 6,360,749 | B1 | | 3/2002 | Jayaraman | |
| 6,986,775 | B2 | * | 1/2006 | Morales et al. | 606/139 |
| 7,311,731 | B2 | | 12/2007 | Lesniak et al. | |
| 2003/0078671 | A1 | | 4/2003 | Lesniak et al. | |
| 2004/0064014 | A1 | | 4/2004 | Melvin et al. | |
| 2005/0080402 | A1 | | 4/2005 | Santamore et al. | |
| 2005/0187620 | A1 | | 8/2005 | Pai et al. | |
| 2006/0025784 | A1 | * | 2/2006 | Starksen et al. | 606/151 |
| 2006/0184242 | A1 | * | 8/2006 | Lichtenstein | 623/2.37 |
| 2006/0241748 | A1 | * | 10/2006 | Lee et al. | 623/2.37 |
| 2010/0030014 | A1 | * | 2/2010 | Ferrazzi | 600/37 |

* cited by examiner

*Primary Examiner* — Katherine Dowe
*Assistant Examiner* — Michael Mendoza (57) ABSTRACT

An endoventricular device includes a backbone and a plurality of segments having a plurality of anchors that are delivered to the treatment site in an inverted delivery configuration within a delivery catheter and when deployed moves from the inverted delivery configuration to a tissue penetrating implantation configuration.

9 Claims, 10 Drawing Sheets

ENDOVENTRICULAR STAY AND DELIVERY SYSTEM

TECHNICAL FIELD

The technical field of this disclosure is medical implant devices, particularly, cardiac implants for treating and preventing dilated cardiomyopathy in heart failure.

BACKGROUND OF THE INVENTION

Coronary heart disease (CHD) is the single leading cause of death in America, where approximately one in five deaths is caused by CHD. CHD causes heart attacks and angina. The most recent available statistics report that over 1.25 million heart attacks occur each year in the United States. A heart attack (myocardial infarction) occurs when the blood supply to part of the myocardium is severely reduced or stopped due to blockage of one or more of the coronary arteries. Heart cells suffer permanent damage or die if the blood supply is cut off for more than a few minutes resulting in damage to the heart muscle (myocardium).

Following myocardial infarction the resulting ischemic damage to the myocardium may lead to a chronic, degenerative spiral of myocardial remodeling that may compromise the ability of the ventricles to provide adequate coronary output. While the process of myocardial remodeling is complex and multifactorial, mechanical strain on the myocardial structure is recognized to contribute to the remodeling process. Relieving this strain would provide means of interrupting the degenerative process.

One approach to relieve the strain has been to reshape or reduce the heart structure by placing bands, cuffs, a jacket or a sock around the exterior of the heart to provide external stress relief to the heart and to reduce the tendency of the myocardium to distend or become permanently stretched and damaged. One drawback to these devices is that each require surgical placement. Another drawback is that these devices, once placed, cover healthy, undamaged tissue and effect change to the entire heart, not just the damaged portion which may lead to valvular dysfunction.

It would be desirable, therefore, to provide a device and a delivery system to relieve the strain through structural reinforcement of the ventricular wall and a method of using the device that would overcome these and other disadvantages.

SUMMARY OF THE INVENTION

One aspect of the present invention provides an endoventricular stay device. The device includes an elongate tubular member having a backbone. The backbone includes a plurality of segments, and a plurality of anchors, the anchors extended perpendicularly from the backbone.

Another aspect of the present invention provides an ventricular stay delivery system. The system includes a delivery catheter having a lumen an endoventricular stay; and a guidewire.

Another aspect of the present invention provides a method of loading and delivering an endoventricular stay. The method includes inverting an endoventricular stay into a delivery configuration, inserting the inverted endoventricular stay into a delivery catheter, inserting a guidewire into a ventricle, advancing a distal end of the delivery catheter over the guidewire and to a ventricle apex, withdrawing the distal end of the delivery catheter, deploying the endoventricular stay from the delivery catheter and withdrawing the guidewire.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION OF PRESENTLY PREFERRED EMBODIMENTS

The invention will now be described by reference to the figures wherein like numbers refer to like structures. The terms "distal" and "proximal" are used herein with reference to the treating clinician during the use of the delivery system; "Distal" indicates an apparatus portion distant from, or a direction away from the clinician and "proximal" indicates an apparatus portion near to, or a direction towards the clinician.

FIGS. 1 to 12 illustrate various embodiments of an endoventricular stay and delivery system in accordance with the present invention.

Figure 1:
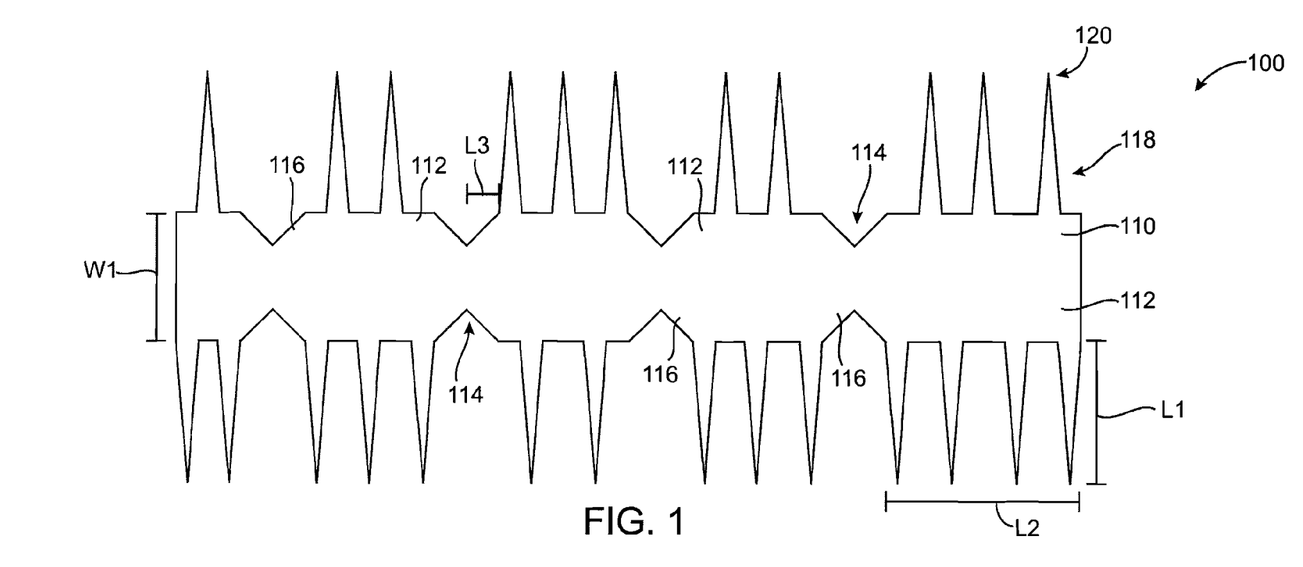
FIG. 1 is a schematic illustration of one embodiment of an endoventricular stay made in accordance with the present invention.
Figure 2A:
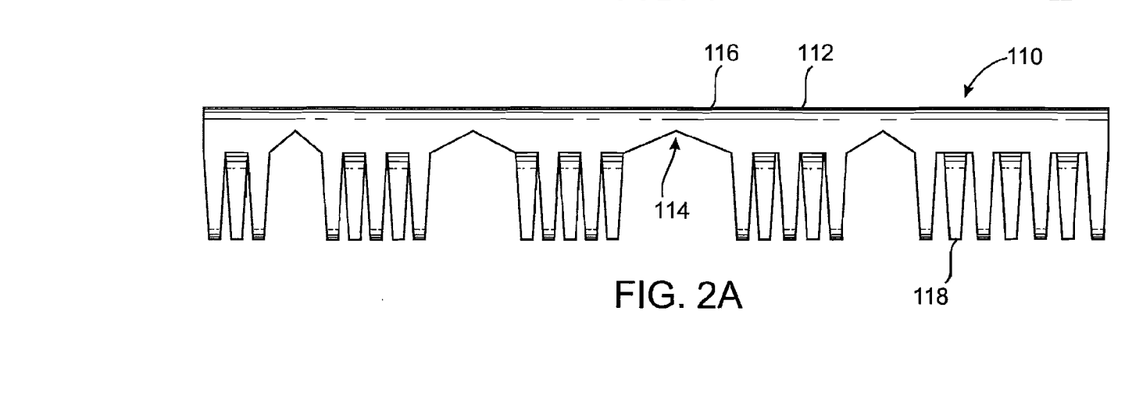
FIG. 2A is a side view of the endoventricular stay of FIG. 1.
Figure 2B:
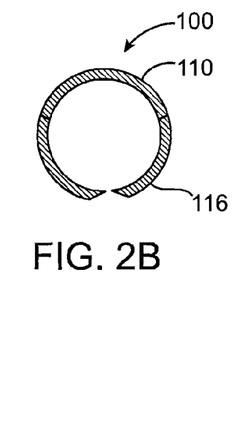
FIG. 2B is an end view of the endoventricular stay shown in FIG. 2A.

FIG. 1 is a schematic illustration of a flattened endoventricular stay 100 made in accordance with the present invention. Endoventricular stay 100 is composed of a shape memory metallic or polymeric material. In one embodiment, endoventricular stay 100 is composed of nitinol. In other embodiments, the chosen material comprises nitinol-like mechanical properties such as the elastic property of nitinol. In one embodiment, endoventricular stay 100 is formed by cutting the stay from a tube of material. The tube of material may be cut using, for example, a laser cutting device. In another embodiment, endoventricular stay 100 is cut from a sheet of material that is then heat set into the implantation configuration (FIG. 2A) of endoventricular stay 100. As shown in FIG. 2B, endoventricular stay 100 includes a circular or substantially circular cross section when in the implantation configuration. In one embodiment, the tube or sheet of material used to form the endoventricular stay has a circumference of approximately 2 cm to 3 cm. Other embodiments have a circumference of approximately 3 cm to 5 cm. The circumference is determined by such factors as the location of implantation and the anatomical dimensions of the organ to be treated.

Endoventricular stay 100 includes a multi-segmented backbone 110 having a plurality of segments 112. Backbone 110 has a width W1 that is about one-third to one-half of the circumference of the endoventricular stay. In one embodiment, width W1 is about 0.5 cm to 1.0 cm. In another embodiment, width W1 is about 1.0 cm to 2.5 cm. The segments 112 of backbone 110 may have substantially similar lengths or may be of varying lengths as shown in FIG. 1. In one embodiment, the overall length of endoventricular stay 100 is divided into segments having segment lengths from about 0.1 cm to 2.5 cm. In another embodiment, the overall length of endoventricular stay 100 is divided into segments having segment lengths L2 from about 0.5 cm to 1.5 cm. Backbone 110 also includes a plurality of articulation points 114. Articulation points 114 are positioned between adjacent segments 112. Articulation points 114 are formed at the junction of tapered portions 116 of the ends of each segment 112. Tapered portions 116 may have a length L3 that is from about 0.1 cm to about 0.5 cm. The articulation points 114 have a length that is approximately one-quarter to one-half of width W1 of backbone 110. In another embodiment, articulation points 114 have a length of 0.25 cm to 1.25 cm. In one embodiment, articulation points 114 have a length of 0.125 cm to 0.5 cm.

Backbone 110 may be divided into any number of segments having variable lengths as determined by such factors as the location of implantation and the anatomical dimensions of the organ to be treated. In one embodiment, an endoventricular stay having an overall length of 7 cm includes a first end segment having a length of about 0.5 cm, a second end segment having a length of about 1.5 cm and three intermediate segments each having a length of about 1.0 cm. In this embodiment, each segment is separated from an adjacent segment by an articulation point and tapered portions having an overall length of about 1.0 cm. In this embodiment, the endoventricular stay is inserted into a delivery catheter so that during deployment the first end segment would be implanted at the ventricular apex and the subsequent segments conform to the anatomy of the ventricular wall.

Endoventricular stay 100 also includes a plurality of anchors 118 extending perpendicularly from each segment 112 of backbone 110. As shown in FIGS. 1 and 2A, the number of anchors extending from each segment may vary according to the overall length L2 of each segment 112. The length L1 of each anchor 118 is approximately one-third of the circumference of the endoventricular stay 110. In one embodiment, the length L1 is about 0.67 cm to about 1.0 cm. In one embodiment, anchors 118 may include additional barbs at the tissue penetrating end 120. The barbs may be the same as or similar to those commonly referred to as fish-hook barbs.

Figure 3:
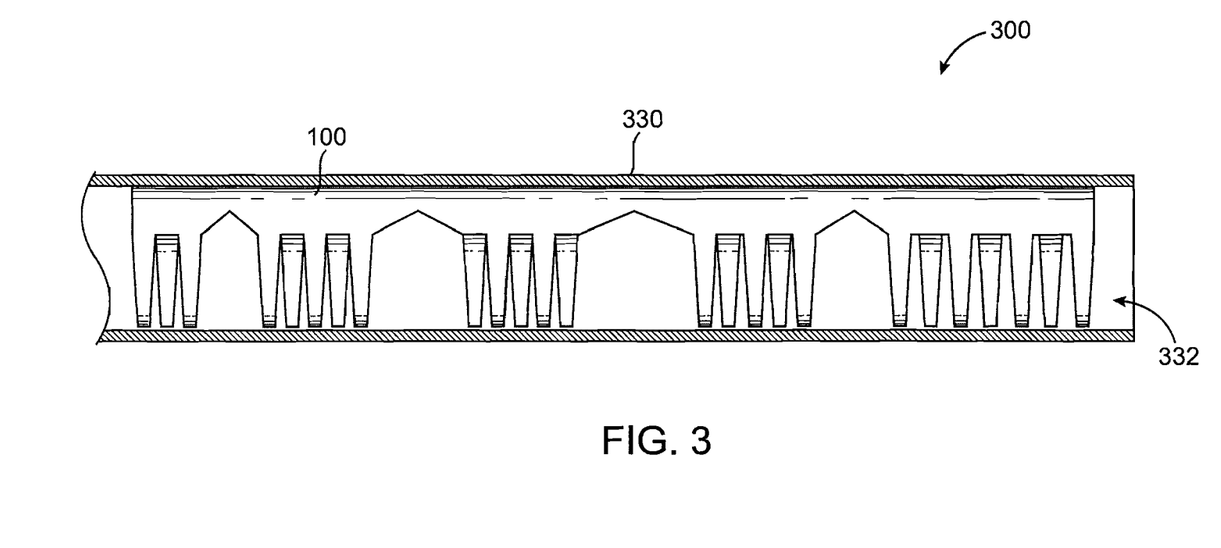
FIG. 3 is a side view of a delivery system for delivering an endoventricular stay made in accordance with the present invention.

FIG. 3 illustrates one embodiment of a delivery system 300 for delivering an endoventricular stay. As shown, endoventricular stay 100 is disposed within a lumen of delivery catheter 330. Catheter 330 comprises an elongated tubular member having a substantially circular cross-section and inside and outside walls that are substantially smooth. Catheter 330 is secured at its proximal end to a fitting and control mechanism 107 for controlling delivery system 300. Catheter 330 may be manufactured from any suitable material such as, for example, a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax® block copolymer, Vestamid® plastic resin, Tecoflex® thermoplastic polyurethanes, Halar® fluoropolymer, Hyflon® fluoropolymers, Pellathane® polyurethane, combinations thereof, and the like. Catheter 330 includes lumen 332 formed therethrough.

Figure 9A:
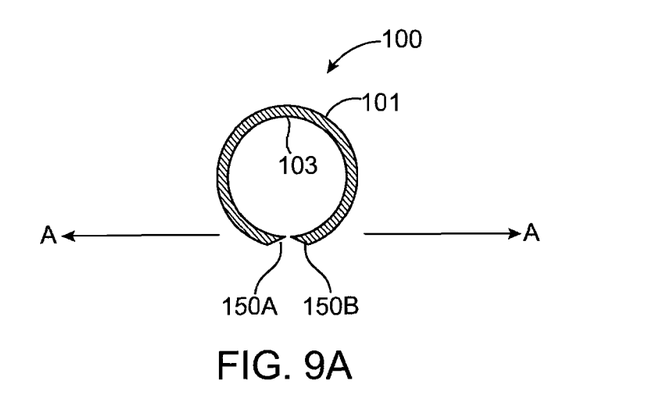
FIGS. 9A to 9C are schematic illustrations showing the loading of an endoventricular stay into a delivery catheter in accordance with the present invention.
Figure 9B:
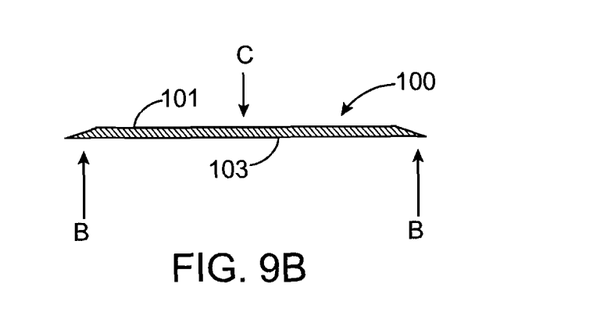
Figure 9C:
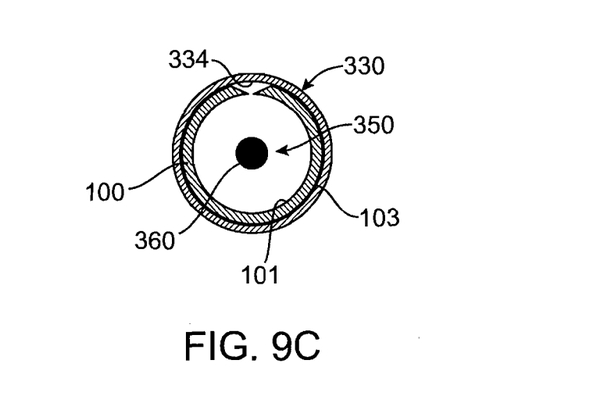

FIGS. 9A to 9C illustrate one embodiment of a method for loading endoventricular stay 100 into the distal end of delivery catheter 330. FIG. 9A illustrates endoventricular stay 100 in the implantation configuration. FIG. 9C illustrates endoventricular stay 100 in an inverted delivery configuration. FIG. 9B illustrates the inversion of endoventricular stay 100 from the implantation configuration to the delivery configuration. To insert endoventricular stay 100 into delivery catheter 330, ends 150A, 150B are drawn apart in the direction of arrows A of FIG. 9A. Next, ends 150A, 150B are moved in the direction of arrows B which moves the outer surface 101 in the direction of arrow C. Continued movement of ends 150A and 150B completely inverts endoventricular stay 100 and places stay 100 in the delivery configuration of FIG. 9C where the inner surface 103 of stay 100 is now on the outside adjacent the inner surface 334 of delivery catheter 330. A central lumen 350 is formed from the inverted stay to allow passage over guidewire 360 during delivery.

Figure 4:
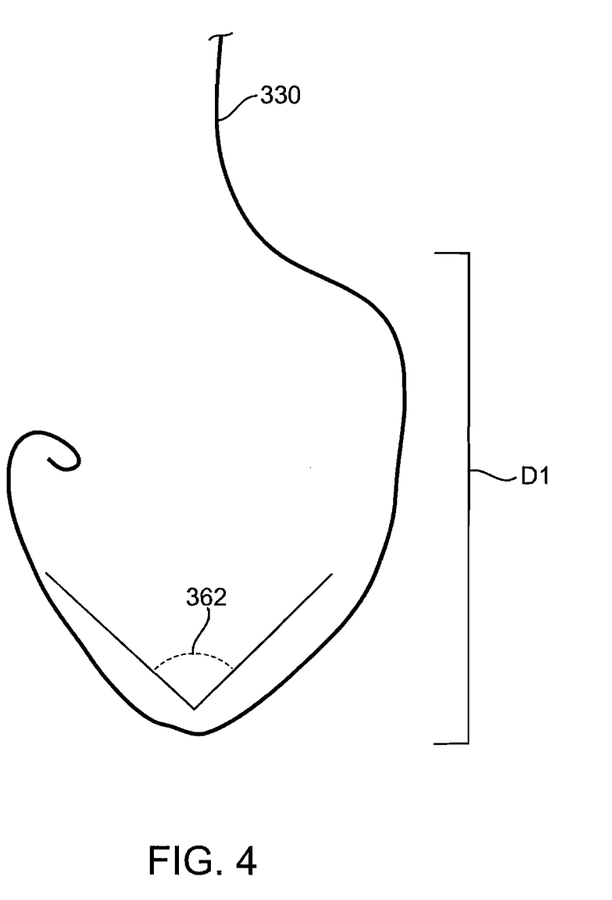
FIGS. 4 to 8 are schematic illustrations of one embodiment of a delivery system and method for implanting an endoventricular stay in accordance with the present invention.
Figure 5:
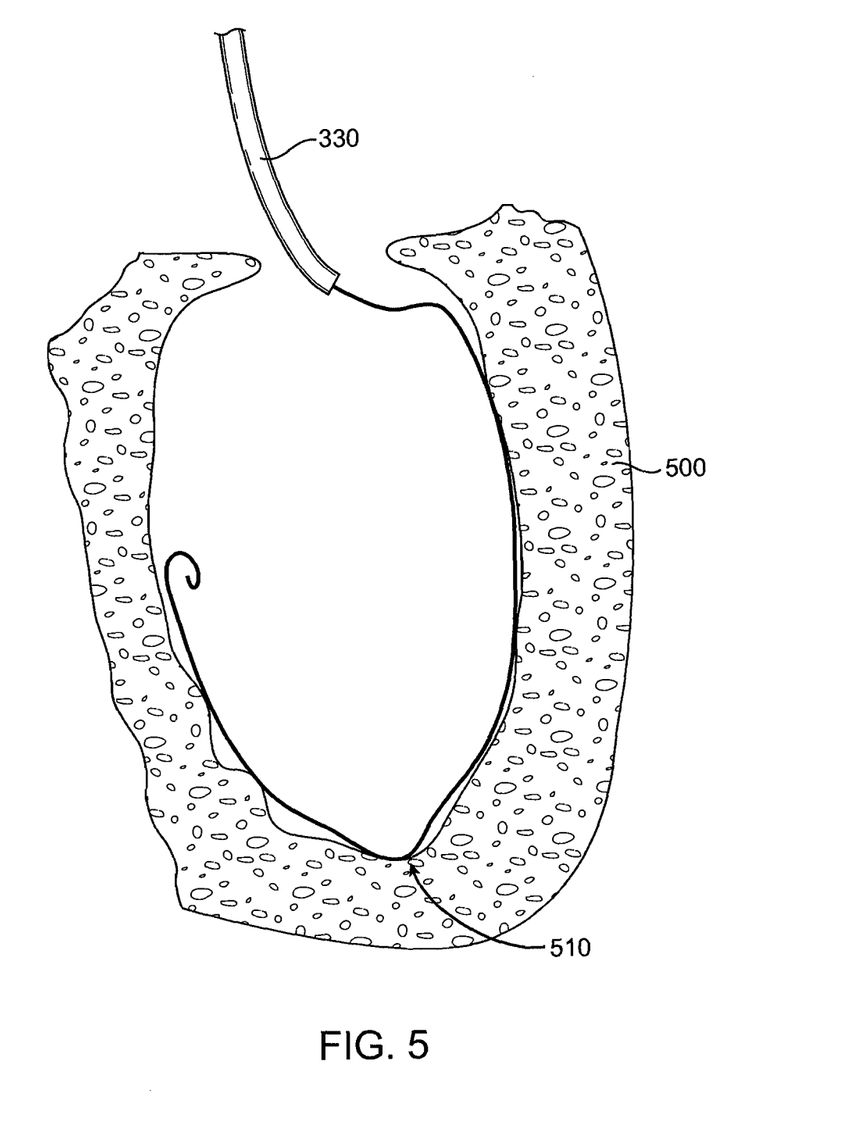

FIG. 4 to 8 further show delivery system 300 and schematically illustrate the delivery and implantation of an endoventricular stay 100 within a left ventricle of the heart. Preferably, the endoventricular stay is advanced to and implanted into the left ventricle using minimally invasive methods. Though not described here, the endoventricular stay may also be implanted using surgical techniques. In FIG. 4 illustrates a guidewire 360 for intra-ventricular delivery and deployment of the endoventricular stay 100. Guidewire 360 is composed of nitinol and is preformed to assume a profile approximating the ventricle anatomy. In one embodiment, guidewire 360 has an insertion dimension D1 of approximately 7 cm. In one embodiment, guidewire 360 is preformed to assume an approximately 50° bend 362 at the apex 510 of the left ventricle 500, as best shown in FIG. 5.

FIG. 5 shows the delivery catheter 330 advancing over guidewire 360. Guidewire 360 has been positioned within ventricle 500 with bend 362 at the apex 510. In one embodiment, the endoventricular stay 100 is advanced through the vascular system to the left ventricle following a pathway from the femoral artery to the aorta and through the aortic valve. In another embodiment, the delivery catheter is advanced over a guidewire that enters the left ventricle through the mitral valve. Endoventricular stay 100 is held in the inverted delivery configuration within delivery catheter 330.

Figure 6:
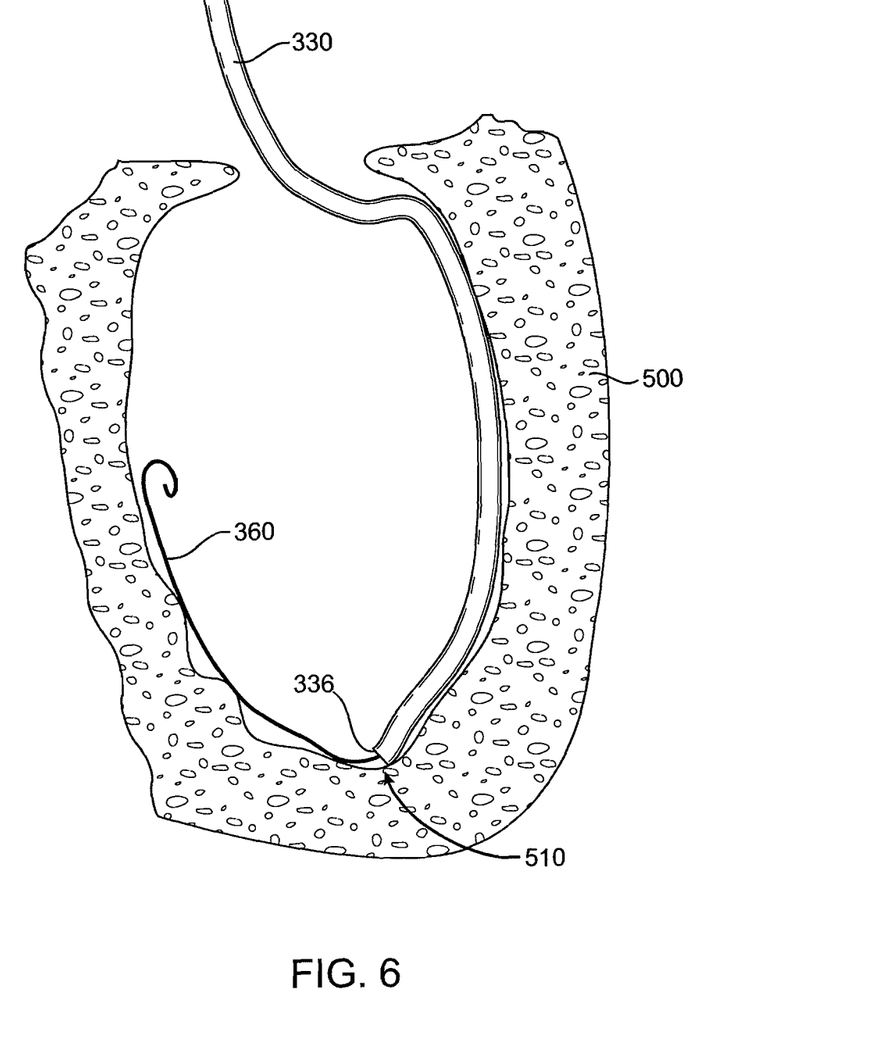
Figure 7:
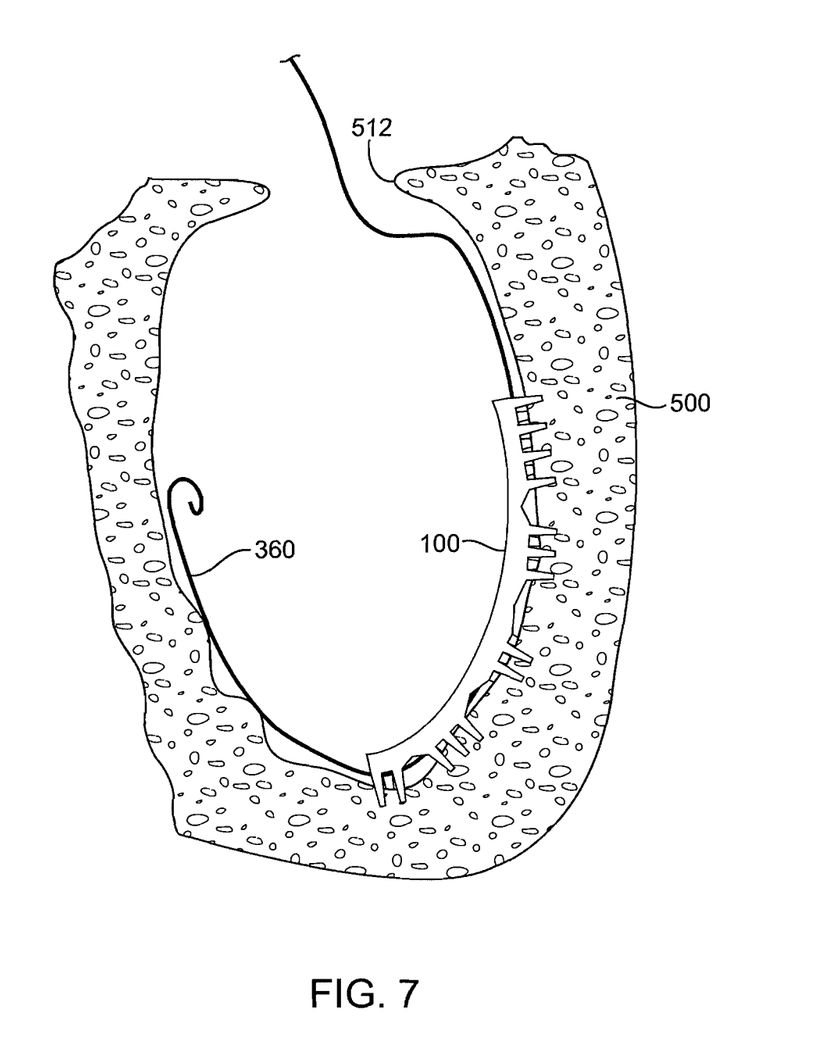
Figure 8:
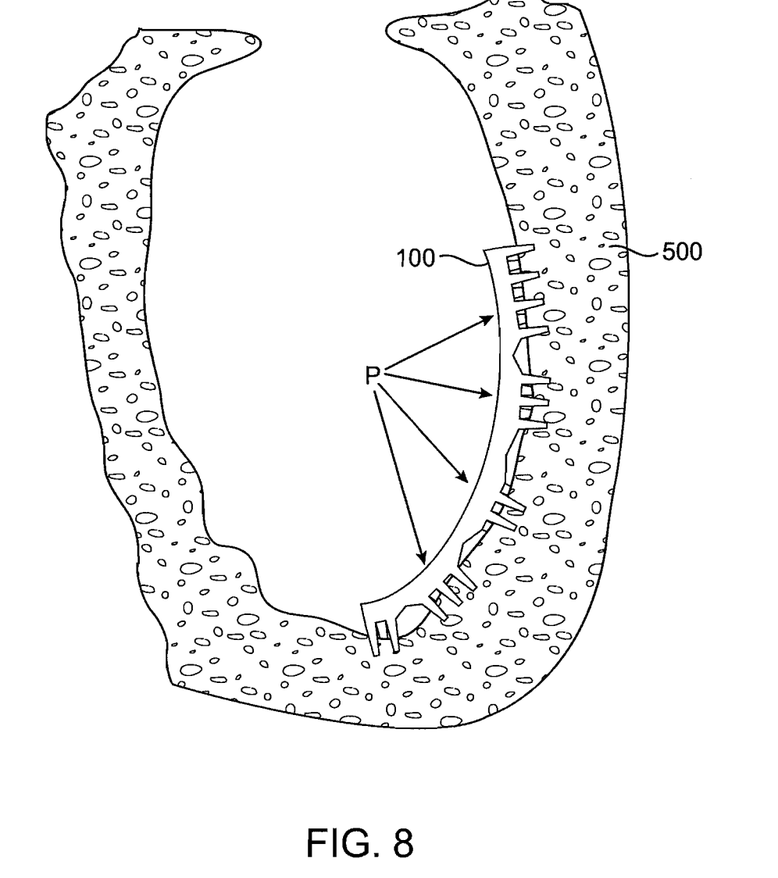

As shown in FIG. 6, delivery catheter 330 is advanced along guidewire 360 until the distal end 336 is resting on the ventricular apex 510. Delivery catheter 330 is then withdrawn while the endoventricular stay 100 is held in place against the ventricular wall 512 on guidewire 360. Withdrawal of delivery catheter 330 in a proximal direction unsheathes the endoventricular stay. As the delivery catheter is withdrawn, each segment unfurls moving from a delivery configuration to an implantation configuration. Each segment is uncovered and implanted prior to uncovering the next segment. Movement of each segment into the implantation configuration causes the tips of the anchors to penetrate the heart tissue as the segment forms the circular stay thereby anchoring the device to the wall of the heart. After the delivery catheter is withdrawn, the guidewire 360 is also withdrawn as seen in FIG. 8. Upon withdrawal of guidewire 360, the stay 100 remains anchored to the myocardium and provides increased rigidity to the ventricle that aids in resisting interior ventricular pressure as depicted by arrows P. Stay 100 further prevents longitudinal stretch of the myocardium. Placement of endoventricular stay is done to not restrict contraction of the remaining functioning (healthy) myocardium. Those with ordinary skill in the art will appreciate that one or more endoventricular stays may be placed as required to treat a particular patient.

Figure 10:
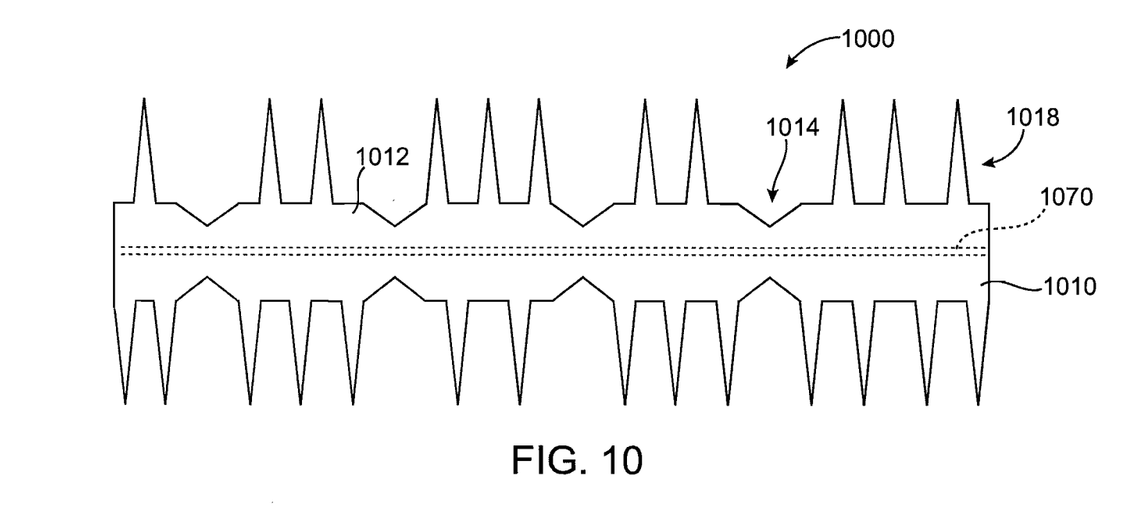
FIG. 10 is a schematic illustration of one embodiment of an endoventricular stay made in accordance with the present invention.
Figure 11A:
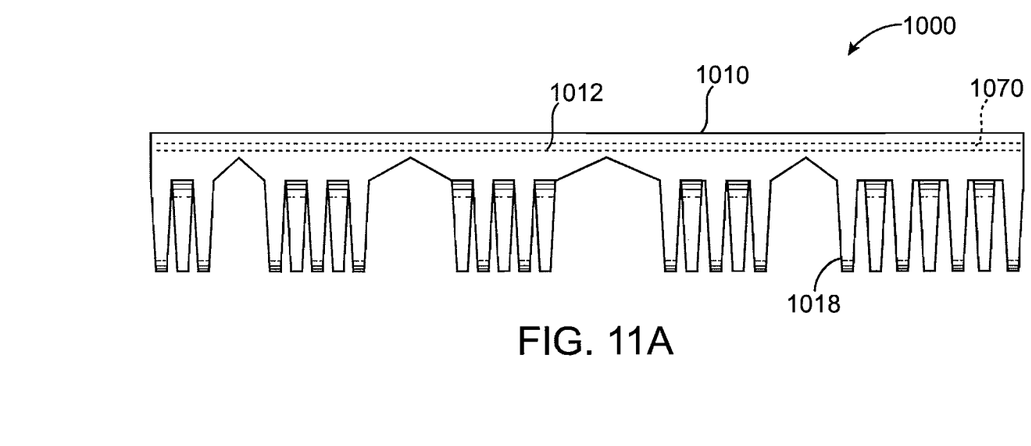
FIG. 11A is a side view of the endoventricular stay of FIG. 10.
Figure 11B:
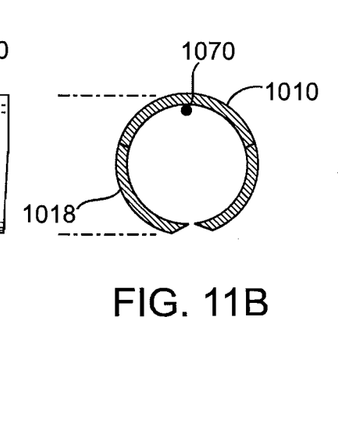
FIG. 11B is an end view of the endoventricular stay shown in FIG. 11A.

FIGS. 10 to 11B illustrate another embodiment of an endoventricular stay 1000 made in accordance with the present invention. Endoventricular stay 1000 is similar to endoventricular stay 100 in many aspects which will not be described here. In this embodiment, endoventricular stay 1000 further includes an elongated backbone reinforcement 1070. Reinforcement 1070 may comprise a filament or wire of a polymeric or metallic material. Reinforcement wire 1070 is attached to or integrally formed with backbone 1010. Reinforcement can extend the entire length of backbone 1010 extending through each segment 1012 and tapered portion 1014. In another embodiment, reinforcement 1070 may be attached to the outer surface of the backbone, instead of the inner surface as best shown in FIGS. 11A and 11B.

Figure 12:
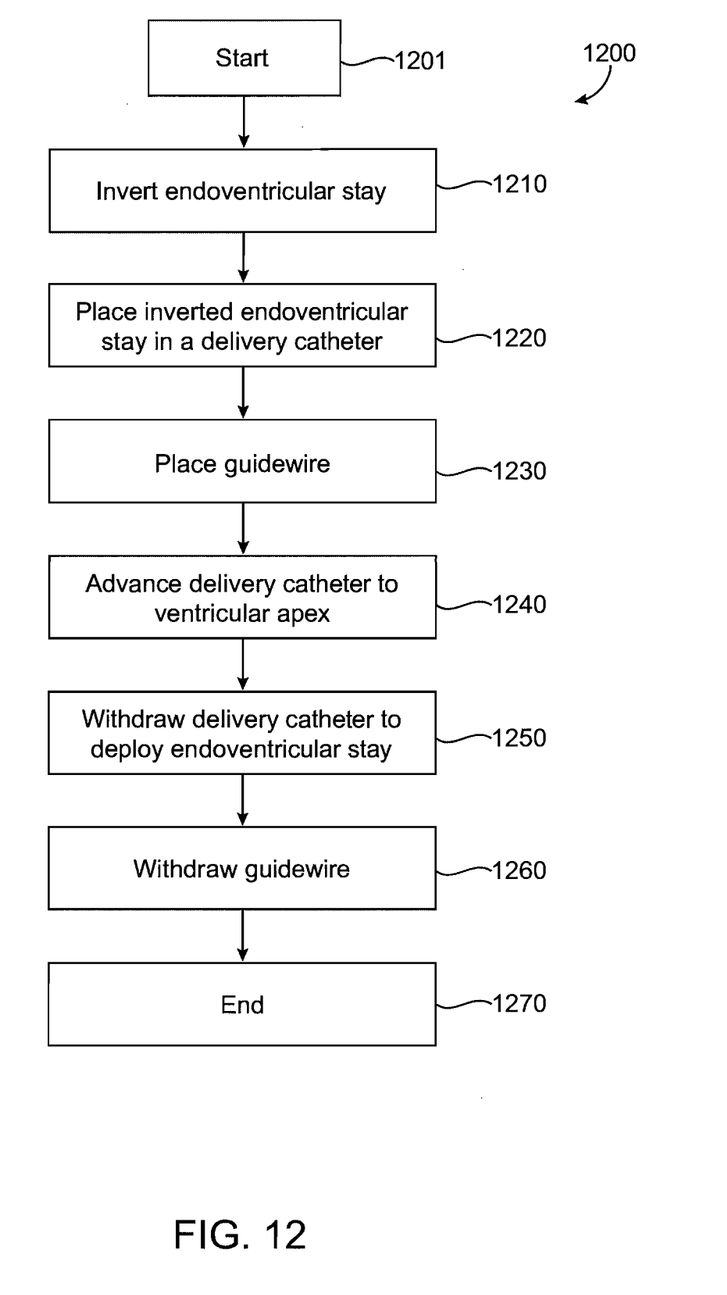
FIG. 12 is a flow chart of a method of loading and delivering an endoventricular stay in accordance with the present invention.

FIG. 12 is a flow chart of one embodiment of a method 2200 of loading and delivering an endoventricular stay, in accordance with the present invention. Method 1200 begins at 1201. Method 1200 may be practiced with endoventricular stays 100 or 1000, described above.

An endoventricular stay is inverted into a delivery configuration as shown in FIGS. 9A to 9C (Block 1210). The inverted endoventricular stay is inserted into a delivery catheter (Block 1220). A guidewire is advanced to the ventricle through the vascular system (Block 1230). The delivery catheter is advanced over the guidewire to place a distal end of the delivery catheter adjacent the ventricular apex (Block 2240). The delivery catheter is withdrawn to deploy each segment of the endoventricular stay in a sequential manner (Block 2250). Deployment of each segment moves each segment from an inverted delivery configuration to the implantation configuration. The guidewire is removed upon complete deployment and implantation of the endoventricular stay. (Block 2260). Method 1200 ends at 1270.

It is important to note that FIGS. 1-12 illustrate specific applications and embodiments of the present invention, and are not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. An endoventricular stay delivery system comprising:
   an elongate delivery catheter having a lumen terminating in an open distal end;
   an elongate tubular stay adapted to be inverted from a) an implantation configuration having a memorized tubular shape with a first surface facing inwardly to b) a tubular delivery configuration constrained within the lumen of the delivery catheter with the first surface facing outwardly, the tubular stay comprising:
   a one-piece backbone extending the entire length of the tubular member, the backbone having first and second ends and a plurality of continuous segments defined therebetween, and
   a plurality of anchors formed integrally with the backbone and, when the tubular member is in the tubular delivery configuration, each anchor extends in a circumferential direction around the tubular member from the backbone to a tissue penetrating end of the anchor.

2. The system of claim 1 wherein
   each segment is separated from an adjacent segment by an articulation point formed at a junction of tapered portions of the ends of each segment, and wherein the articulation point extends perpendicular to the backbone for a length that is approximately one-quarter to one-half of the width of the backbone.

3. The system of claim 1 wherein the plurality of segments includes a first end segment having a first length and a second end segment having a second length wherein the first length is less than the second length.

4. The system of claim 3 wherein the backbone includes a plurality of segments having a third length and being disposed between the first end segment and the second end segment, wherein the third length is greater than the first length and less than the second length.

5. The system of claim 4 wherein the first length is 0.5 cm, the second length is 1.5 cm and the third length is 1.0 cm.

6. The system of claim 1 wherein the elongated tubular stay is composed of nitinol.

7. The system of claim 1 wherein at least a portion of the anchors include at least one barb disposed at the tissue penetrating end of the anchor.

8. The system of claim 1 further comprising a reinforcement member disposed along at least a portion of the backbone.

9. The system of claim 1 wherein, when the tubular stay is in the implantation configuration, none of the tissue penetrating ends of the anchors overlaps each other.

* * * * *